(12) United States Patent
Okagami et al.

(10) Patent No.: US 9,810,836 B2
(45) Date of Patent: Nov. 7, 2017

(54) EXTERNAL TUBE, LASER TRANSMISSION PATH, AND LASER TREATMENT TOOL

(75) Inventors: Yoshihide Okagami, Kyoto (JP); Mikinori Nishimura, Kyoto (JP); Yoshiteru Tamura, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 13/469,774

(22) Filed: May 11, 2012

(65) Prior Publication Data

US 2012/0289949 A1 Nov. 15, 2012

(30) Foreign Application Priority Data

May 11, 2011 (JP) .................................. 2011-106516
May 11, 2011 (JP) .................................. 2011-106517

(51) Int. Cl.
*A61B 18/22* (2006.01)
*F21V 8/00* (2006.01)
(Continued)

(52) U.S. Cl.
CPC ........ *G02B 6/0096* (2013.01); *A61B 1/00165* (2013.01); *A61B 1/018* (2013.01);
(Continued)

(58) Field of Classification Search
CPC .. A61B 18/18; A61B 1/00; A61B 1/04; A61B 1/12; A61B 1/06; A61B 5/05;
(Continued)

(56) References Cited

U.S. PATENT DOCUMENTS 4,207,874 A * 6/1980 Choy ............................ 600/108
4,583,539 A * 4/1986 Karlin et al. ..................... 606/4
(Continued)

FOREIGN PATENT DOCUMENTS

JP S57-029202 B2 2/1982
JP S59-1003 U 1/1984
(Continued)

OTHER PUBLICATIONS

The American Heritage® Dictionary of the English Language, Fourth Edition copyright © 2000 by Houghton Mifflin Company. Updated in 2009. Published by Houghton Mifflin Company.*
(Continued)

*Primary Examiner* — Adam J Eiseman
*Assistant Examiner* — Victor Shapiro
(74) *Attorney, Agent, or Firm* — Osha Liang LLP

(57) ABSTRACT

An object is to provide a laser treatment tool capable of guiding a plurality of fluids, a laser transmission path insertable into such a laser treatment tool, and an external tube for forming the laser transmission path. In an external tube 80 which forms a laser transmission path 70 together with a lengthy hollow waveguide path 90 for guiding treatment laser light 57a and has an inner insertion space 81 for allowing insertion of the hollow waveguide path 90, a plurality of sub passages 84 and cooling water passages 85 are provided outside the hollow waveguide path 90, inserted into the insertion space 81, along a longitudinal direction of the insertion space 81.

17 Claims, 6 Drawing Sheets

(51) Int. Cl.
  *A61B 1/00* (2006.01)
  *A61B 1/018* (2006.01)
  *A61B 18/20* (2006.01)
  *G02B 23/24* (2006.01)
  *A61B 18/00* (2006.01)

(52) U.S. Cl.
  CPC ............ *A61B 18/201* (2013.01); *A61B 18/22* (2013.01); *G02B 23/2476* (2013.01); *A61B 2018/00023* (2013.01); *A61B 2218/002* (2013.01)

(58) Field of Classification Search
  CPC . A61B 6/00; A01N 63/00; A61N 5/06; B05D 5/06
  USPC ....... 600/104, 156, 160, 173, 478, 108, 407, 600/463; 606/3, 4, 10, 14, 7, 41; 607/88; 427/163.2; 424/93.21; 356/479
  See application file for complete search history.

(56) References Cited

U.S. PATENT DOCUMENTS

| | | | | |
|---|---|---|---|---|
| 4,917,083 | A * | 4/1990 | Harrington et al. | 606/15 |
| 5,074,860 | A * | 12/1991 | Gregory et al. | 606/14 |
| 5,150,373 | A | 9/1992 | Kolb et al. | |
| 5,312,398 | A * | 5/1994 | Hobart et al. | 606/14 |
| 5,318,024 | A * | 6/1994 | Kittrell et al. | 600/478 |
| 5,567,471 | A * | 10/1996 | Harrington et al. | 427/163.2 |
| 5,672,171 | A * | 9/1997 | Andrus et al. | 606/15 |
| 5,746,736 | A * | 5/1998 | Tankovich | 606/9 |
| 5,876,426 | A * | 3/1999 | Kume et al. | 607/88 |
| 5,928,137 | A * | 7/1999 | Green | 600/160 |
| 5,951,543 | A * | 9/1999 | Brauer | 606/10 |
| 6,368,318 | B1 * | 4/2002 | Visuri et al. | 606/7 |
| 6,554,793 | B1 * | 4/2003 | Pauker et al. | 604/95.01 |
| 6,712,759 | B2 * | 3/2004 | Muller | 600/156 |
| 7,158,234 | B2 * | 1/2007 | Uchiyama | A61B 1/0008 356/479 |
| 7,448,995 | B2 * | 11/2008 | Wiklof et al. | 600/173 |
| 7,922,650 | B2 * | 4/2011 | McWeeney et al. | 600/104 |
| 7,988,689 | B2 * | 8/2011 | Woloszko et al. | 606/41 |
| 2002/0068924 | A1 * | 6/2002 | Sinofsky | 606/3 |
| 2003/0100824 | A1 * | 5/2003 | Warren et al. | 600/407 |
| 2003/0118563 | A1 * | 6/2003 | Loeb | 424/93.21 |
| 2004/0179796 | A1 | 9/2004 | Jakobsen et al. | |
| 2006/0052661 | A1 * | 3/2006 | Gannot et al. | 600/108 |
| 2010/0249601 | A1 * | 9/2010 | Courtney | A61B 5/0066 600/463 |
| 2011/0105845 | A1 * | 5/2011 | Gordon et al. | 600/156 |

FOREIGN PATENT DOCUMENTS

| | | |
|---|---|---|
| JP | 62-148675 A | 7/1987 |
| JP | 03-001104 A | 1/1991 |
| JP | H11-194068 A | 7/1999 |
| JP | 2001-046388 A | 2/2001 |
| JP | 2006-341066 A | 12/2006 |
| JP | 2007-533374 A | 11/2007 |

OTHER PUBLICATIONS

Haswell, Charles Haynes (1920). Mechanics' and Engineers' Pocket-book of Tables, Rules, and Formulas. Harper & Brothers. Retrieved Apr. 9, 2007.*

* cited by examiner

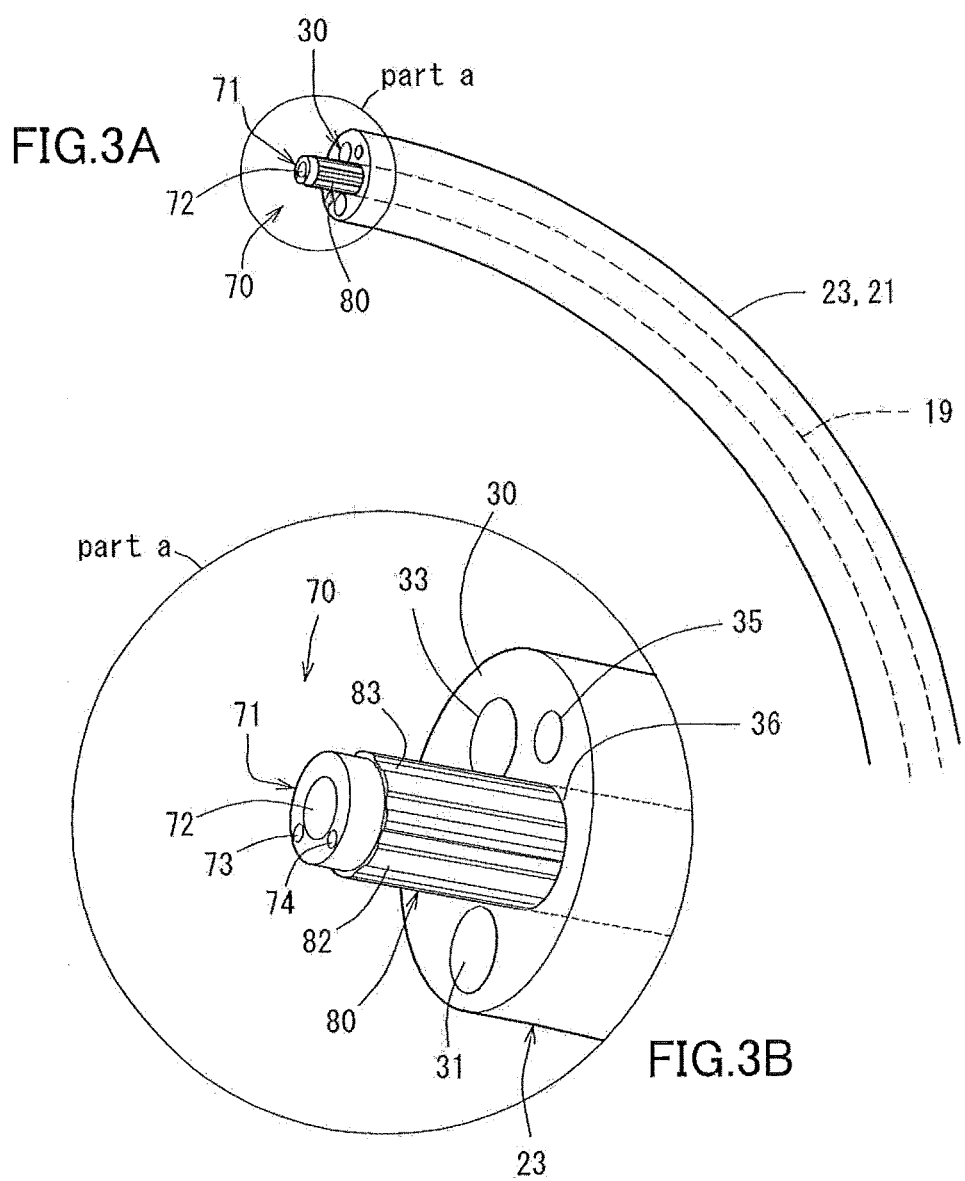

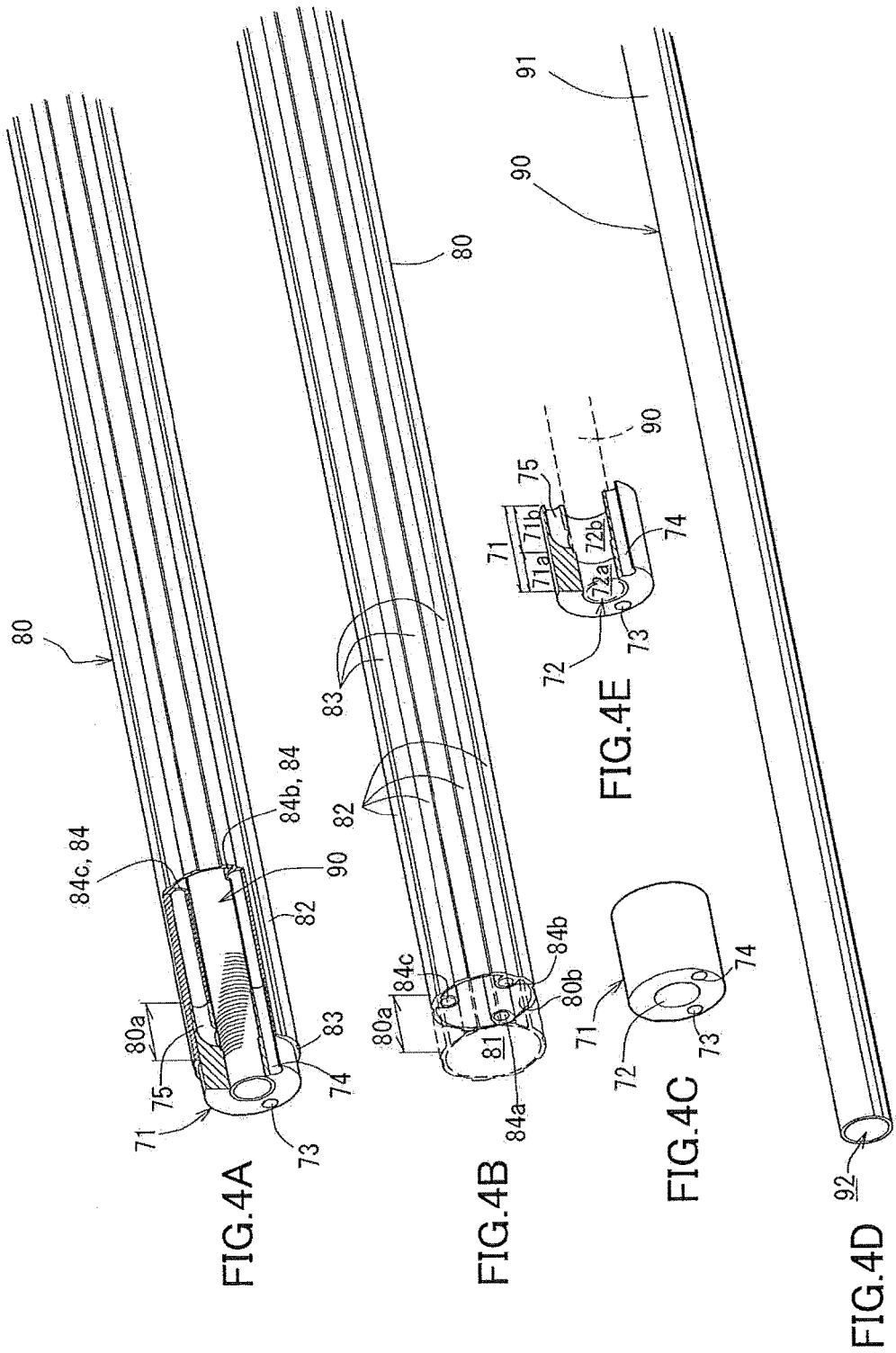

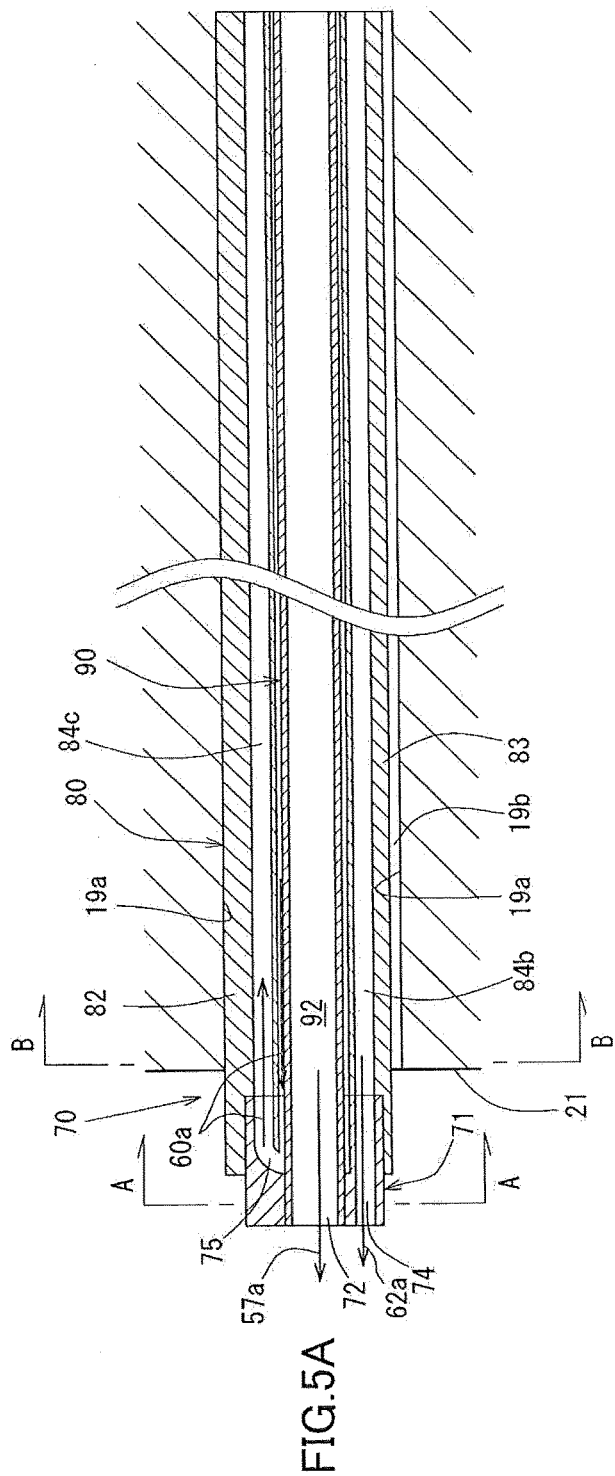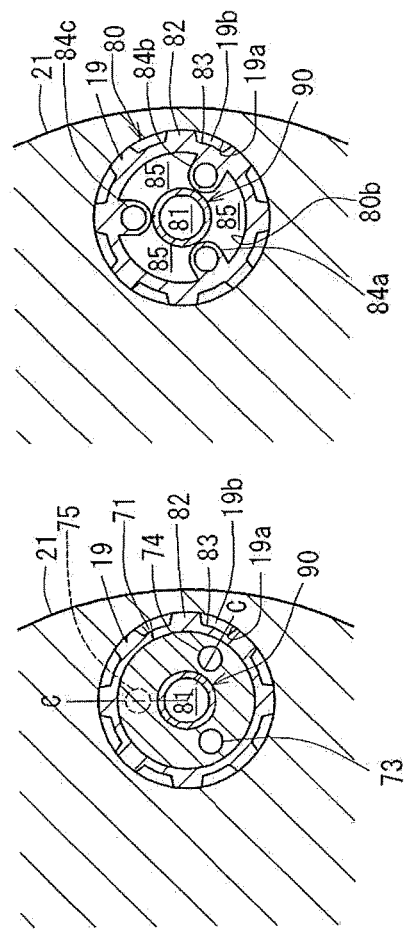

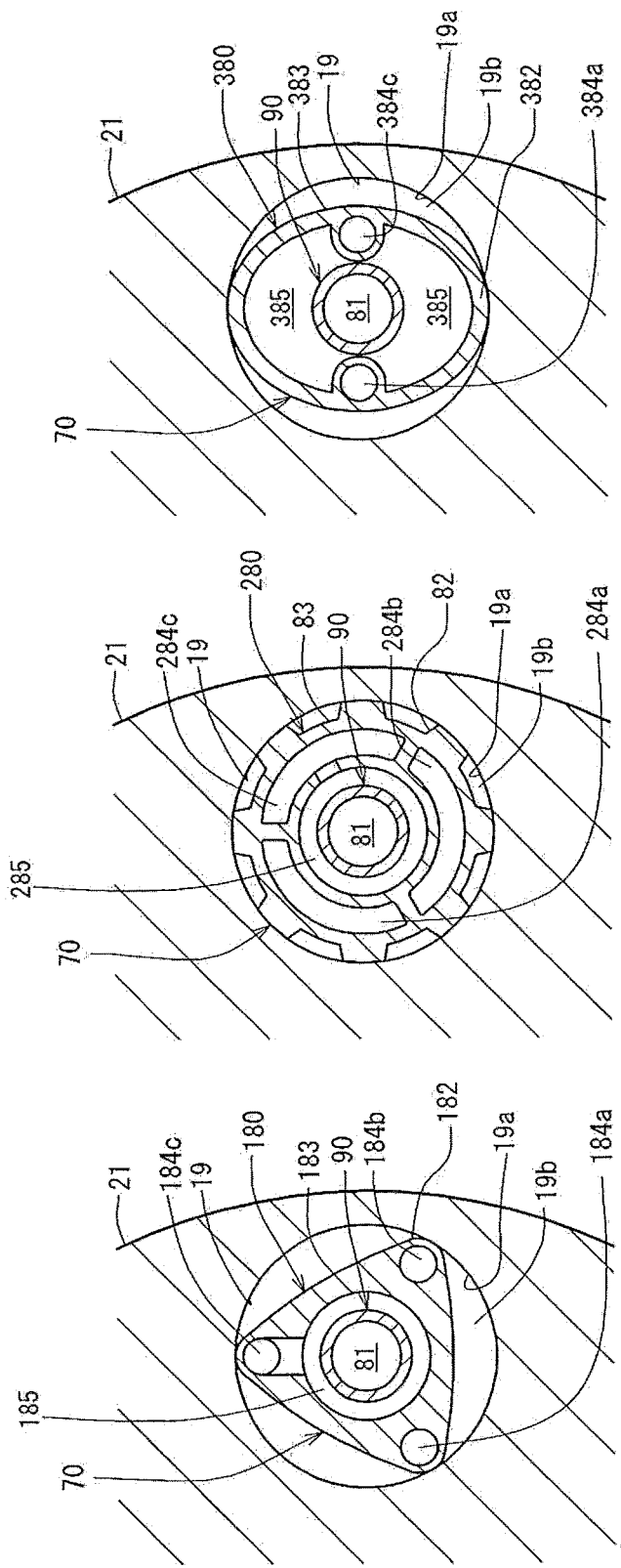

EXTERNAL TUBE, LASER TRANSMISSION PATH, AND LASER TREATMENT TOOL

BACKGROUND OF THE INVENTION

1. Field of the Invention

The present invention relates to a laser treatment tool for, for example, performing a laser treatment, a laser transmission path insertable into the laser treatment tool, and an external tube for forming the laser transmission path.

2. Description of the Prior Art

Conventionally, a treatment method using an endoscope is used as a treatment method capable of providing a treatment with little burden on a patient. According to such a treatment using an endoscope, an endoscope tube is inserted into the body from the oral cavity or the like, and imaging or a surgical operation is performed by use of a tip structure section of the endoscope tube.

Imaging is performed as follows. Illumination light is provided from the tip structure section, and the illumination light reflected by a body tissue is received by a lens provided in the tip structure section and transmitted from the endoscope tube to an endoscope main body device. The endoscope main body device puts the light into an image and displays the image on a display device. Alternatively, imaging is performed as follows. An image is shot by an imaging element such as a CCD sensor or the like provided in the tip structure section of the endoscope tube, and an image signal formed by the tip structure section is transmitted via the endoscope tube to the endoscope main body device. Then, an image is displayed on the display device.

A surgical operation is performed by a tip of appropriate forceps which are inserted from a forceps insertion opening called a "channel" and coming out from a forceps exit in the tip structure section. As the forceps, any of various tools including holding forceps, a knife and the like can be usable.

As a tool insertable from the forceps insertion opening and usable for a surgical operation, a tool using a laser transmission path for providing laser light for treatment (herein after, referred to as the "treatment laser light") has been proposed (see Patent Document 1). The laser transmission path in Patent Document 1 is described as guiding gas such as carbon dioxide or the like, together with $CO_2$ laser light, through a hollow tube-like waveguide path (herein after, referred to as the "hollow waveguide path").

The gas guided through the hollow waveguide path is described as acting as a cooling fluid for cooling the hollow waveguide path which has been heated by the laser light.

As a structure of a laser transmission device which uses a carbon dioxide laser and is usable for a processing device, a structure including a water passage in an outer part thereof for cooling the hollow waveguide path for transmitting carbon dioxide laser light has been proposed (see Patent Document 2).

In a cauterization operation performed by use of a laser for treatment, especially in endoscopic submucosal dissection (ESD) or endoscopic mucosal resection (EMR), it is required to eject assist gas or physiological saline solution in order to securely obtain a visual field by expanding an operation target space and by removing transpired substances or fumes, or to recover cooling water which has been used to cool the hollow waveguide path. However, there has not been a structure for realizing both of the ejection of the assist gas or the physiological saline solution and the recovery of the cooling water with one laser transmission path.

PRIOR ART DOCUMENT

Patent Document

Patent Document 1: PCT Japanese National-Phase Laid-Open Patent Publication No. 2007-533374
Patent Document 2: Japanese Laid-Open Patent Publication No. Hei 03-001104

SUMMARY OF THE INVENTION

Problems to be Solved by the Invention

In light of the above-described problems, the present invention has an object of providing a laser treatment tool capable of guiding a plurality of fluids, a laser transmission path insertable into such a laser treatment tool, and an external tube for forming the laser transmission path.

Means for Solving the Invention

The present invention is directed to an external tube for forming a laser transmission path together with a lengthy hollow waveguide path for guiding laser light, the external tube having an inner insertion hole for allowing insertion of the hollow waveguide path, wherein the external tube includes a plurality of fluid passages located outside the hollow waveguide path, inserted into the insertion hole, along a longitudinal direction of the insertion hole.

The hollow waveguide path may be formed as follows. A tubular member is formed of a material having a highly smooth surface, for example, glass or the like. On an inner wall of the tubular member, a reflective film of silver or the like is formed. Then, on an inner surface of the reflective film, a dielectric thin film is formed of a material having a high transmission efficiency such as a cyclic olefin polymer, polyimide or the like.

A laser transmission path formed by use of such an external tube according to the present invention can guide a plurality of fluids.

This will be described in more detail. The plurality of fluid passages are provided outside the hollow waveguide path along the longitudinal direction of the insertion hole. Owing to this, appropriate fluids are guided through the plurality of passages, for example, a guide passage for cooling water, a water recovery passage for recovering the cooling water, a passage for assist gas, a passage for irrigation, and the like. Thus, a plurality of desired fluids can be guided.

In an embodiment of the present invention, the plurality fluid passages may be located between the hollow waveguide path inserted into the insertion hole and an inner surface of the insertion hole, at an equal interval with respect to the inner surface.

According to the present invention, the hollow waveguide path inserted into the insertion hole inside the external tube can be positioned at the center of the external tube with certainty, and a space enclosed by the plurality of fluid passages located at an equal interval and an outer circumferential surface of the hollow waveguide path can act as a passage.

In an embodiment of the present invention, the external tube may be inserted into a transmission path insertion hole of an endoscope external hose. The external tube may further include projections located at least at two positions as seen in a cross-section of the external tube and projecting outward in a radial direction such that in the state where the external tube is inserted into the transmission path insertion hole, tips of the projections are in contact with an inner surface of the transmission path insertion hole; and gap formation parts for forming gaps together with the inner surface of the transmission path insertion hole, the gaps being formed between adjacent projections of the at least two projections.

According to the present invention, an external tube included in a laser treatment tool which can inhale fumes in ESD or EMR can be provided.

This will be described in more detail. In a cauterization operation performed by use of a laser for treatment, especially in endoscopic submucosal dissection (ESD) or endoscopic mucosal resection (EMR), it is required to remove fumes in order to expand the operation target space and also to securely obtain a visual field.

For example, Japanese Laid-Open Patent Publication No. 62-148675 proposes a body cavity inner pressure adjusting device of a laser treatment device. According to this body cavity inner pressure adjusting device, an absorption tube is communicated to a gap between a protective pipe of a laser transmission fiber and a forceps channel and the gap is used as an absorption channel.

Japanese Laid-Open Patent Publication No. 2006-341066 proposes a medical treatment tool usable with an endoscope. This medical treatment tool includes a flow path for a supplied fluid or an absorbed fluid, between an outer circumferential surface of an insertion section and an inner circumferential surface of a sheath.

As described above, a laser transmission path usable in a cauterization operation performed by use of a laser for treatment, especially in endoscopic submucosal dissection (ESD) or endoscopic mucosal resection (EMR), is required to have various functions of performing irrigation, ejecting assist gas, cooling the hollow waveguide path and the like. Therefore, such a laser transmission path has a complicated cross-sectional structure and has a larger diameter than the diameter of the laser transmission paths used in the past.

The laser transmission path has such a larger diameter, and thus cannot adopt the structure described in any of the above-identified patent documents to inhale fumes in ESD or EMR in the state where the laser transmission path is inserted into the transmission path insertion hole of an endoscope external hose.

However, according to the present invention, the external tube is used to form the laser transmission path, and the laser transmission path formed by use of the external tube is inserted into the transmission path insertion hole of the endoscope external hose included in the laser treatment tool. Owing to this, the fumes are inhaled by the gap formation parts. In a cauterization operation performed by use of laser light, especially in endoscopic submucosal dissection (ESD) or endoscopic mucosal resection (EMR), the operation target site can be expanded and also the visual field can be securely obtained. Therefore, reliable and safe surgical operations can be performed.

The laser transmission path formed by use of the external tube according to the present invention is inserted into the transmission path insertion hole of the endoscope external hose included in the laser treatment tool. Owing to this, the laser transmission path can be positioned at the center of the transmission path insertion hole.

In an embodiment of the present invention, the external tube may include a plurality of convexed and concaved parts located continuously in a circumferential direction of the external tube so as to have a gear-like cross-section; and the convexed and concaved parts may form the projections and the gap formation parts.

The convexed and concaved parts may be formed of a curved line, instead of being formed of apexes and sides.

According to the present invention, the laser transmission path formed by use of the external tube according to the present invention can be positioned at the center of the transmission path insertion hole with more certainty. In addition, the concaved gap formation parts formed along the circumferential direction of the external tube can absorb fumes.

In an embodiment of the present invention, the external tube may have a polygonal cross-section; and apexes of the polygonal cross-section may form the projections, and sides of the polygonal cross-section may form the gap formation parts.

The "polygonal cross-section" represents a concept encompassing, for example, a polygonal cross-section formed of apexes and sides such as a triangular or square cross-section, and also a generally polygonal cross-section formed of a curved line having an inflection point.

According to the present invention, the laser transmission path formed by use of the external tube according to the present invention can be positioned at the center of the transmission path insertion hole with more certainty. In addition, the concaved gap formation parts formed by the sides of the polygonal cross-section can absorb fumes.

In an embodiment of the present invention, the external tube may have an elliptical cross-section; and arcked parts at ends of a longer axis of the elliptical cross-section may form the projections, and arcked parts at ends of a shorter axis of the elliptical cross-section may form the gap formation parts.

According to the present invention, the laser transmission path formed by use of the external tube according to the present invention can be positioned at the center of the transmission path insertion hole. In addition, the concaved gap formation parts formed by the arcked parts at ends of the shorter axis of the elliptical cross-section can absorb fumes.

The present invention is also directed to a laser transmission path including the hollow waveguide path inserted into the insertion hole of the above-described external tube.

According to the present invention, the plurality of fluids can be guided to treat the operation target site with laser light with certainty.

This will be described in more detail. The hollow waveguide path is inserted into the insertion hole of the external tube. Owing to this, appropriate fluids are guided through the plurality of passages provided outside the hollow waveguide path along the longitudinal direction of the insertion hole, for example, a guide passage for cooling water, a water recovery passage for recovering cooling water, a passage for assist gas, a passage for irrigation, and the like. Thus, while a plurality of desired fluids are guided, the operation target site can be treated with the laser light with certainty.

In an embodiment of the present invention, one of the plurality of fluid passages may be a cooling water passage for supplying cooling water for cooling the hollow waveguide path such that the cooling water flows in a direction in which the laser light is directed.

The cooling water may be physiological saline solution, fresh water or the like.

According to the present invention, the hollow waveguide path which has been heated by the laser light can be cooled by the cooling water flowing in the fluid passage. Therefore, the laser transmission path for providing laser light for treating the operation target site with certainty can be improved in durability.

In an embodiment of the present invention, one of the plurality of fluid passages which is different from the cooling water passage may be a cooling water recovery passage for allowing the cooling water which has cooled the hollow waveguide path to flow in a direction opposite to the direction in which the laser light is directed, and thus recovering the cooling water.

According to the present invention, the cooling water can be recovered. Therefore, the cooling water can be circulated, and the hollow waveguide path which has been heated by the laser light can be cooled efficiently.

The cooling water can be circulated in the cooling water passage and the cooling water recovery passage without leaking to the operation target site.

In an embodiment of the present invention, one of the plurality of fluid passages which is different from the cooling water passage may be an irrigation passage for supplying irrigation water such that the irrigation water flows in the direction in which the laser light is directed and is released toward a diseased part.

The irrigation water released toward the operation target site (diseased part) may be physiological saline solution.

According to the present invention, while the hollow waveguide path which has been heated is cooled by the cooling water, irrigation water is released toward the operation target site (diseased part) in the body such as the wall of esophagus, the wall of stomach wall or the like. Owing to this, while the treatment space is expanded to, for example, securely obtain the visual field, the operation target site (diseased part) can be treated with the laser light with certainty.

In an embodiment of the present invention, one of the plurality of fluid passages which is different from the cooling water passage may be an assist gas passage for supplying assist gas such that the assist gas flows in the direction in which the laser light is directed and is released toward the diseased part.

The assist gas may be, for example, an appropriate gas such as carbon dioxide or the like which is more absorbable in the body than air.

According to the present invention, while the hollow waveguide path which has been heated is cooled by the cooling water, the assist gas is guided and is ejected toward the operation target site in the body such as the wall of esophagus, the wall of stomach or the like. Owing to this, while the treatment space is expanded and also the fumes are removed to, for example, securely obtain the visual field, the operation target site can be treated with the laser light with certainty.

In the case where the assist gas is, for example, an appropriate gas such as carbon dioxide or the like which is more absorbable in the body than air, the following advantage is provided. According to the present invention, the laser light is guided through the hollow waveguide path, and the assist gas is guided through the assist gas passage which is outside the hollow waveguide path and inside the external tube. Namely, the laser light and the assist gas are guided through separate guide paths. Therefore, an inconvenience which would occur in the case where the laser light and the assist gas are guided through the same guide path, namely, the inconvenience that the laser light is absorbed by the assist gas and as a result, the operation target site cannot be irradiated with laser light of a desired output, does not occur. Thus, reduction of the transmission efficiency of the laser light which would be caused by such an inconvenience can be prevented. The laser light and the assist gas are guided without the transmission efficiency of the laser light being reduced, and the assist gas is ejected toward the operation target site in the body such as the wall of esophagus, the wall of stomach or the like. Owing to this, while the treatment space is expanded and also the fumes are removed to, for example, securely obtain the visual field, the operation target site can be treated with the laser light with certainty.

In other words, the freedom degree of combination of the assist gas and the laser light is increased. As a result, the convenience is improved.

The present invention is also directed to a laser transmission path including the hollow waveguide path inserted into the insertion hole of the above-described external tube including the outer projections and the gap formation parts.

According to the present invention, the fumes are inhaled by the gap formation parts, and the operation target site can be treated with the laser light with certainty.

The present invention is also directed to a laser treatment tool including a laser generation source; a laser control section; and the above-described laser transmission path. The laser transmission path is inserted into a transmission path insertion hole of an endoscope external hose, and a tip of the laser transmission path is located in the vicinity of a tip opening of the endoscope external hose.

Owing to this, the tip of the laser transmission path for providing the laser light can be guided to the operation target site with certainty.

This will be described in more detail. Usually, the endoscope external hose includes a plurality of channels, and one of the channels includes an image fiber. The image fiber has a CCD camera at an end thereof on the side of a main body. Alternatively, the image fiber has a CCD camera at a tip of the channel on the side of a diseased part. Therefore, the operator can allow the tip of the endoscope external hose to reach the operation target site while checking an image shot by the CCD camera. Hence, the tip of the laser transmission path inserted into the endoscope external hose and located in the vicinity of the tip opening of the endoscope external hose can be guided to a position very close to the operation target site with certainty. Therefore, the assist gas or irrigation water can be ejected toward the operation target site in the body such as the wall of esophagus, the wall of stomach or the like. Thus, the treatment space is expanded and also the fumes are removed to, for example, securely obtain the visual field, and also the operation target site can be treated with laser light with more certainty while the hollow waveguide path which has been heated is cooled by the cooling water.

The present invention is also directed to a laser treatment tool including a laser generation source; a laser control section; and the above-described laser transmission path. The laser transmission path is inserted into a transmission path insertion hole of an endoscope external hose such that a tip of the laser transmission path is located in the vicinity of a tip opening of the endoscope external hose; and a fluid inhalation unit is connected to the gap formation parts, and the gap formation parts each form a fluid absorption passage.

Owing to this, the tip of the laser transmission path for providing the laser light can be guided to the operation target site with certainty.

In an embodiment of the present invention, the laser light may be carbon dioxide laser light.

According to the present invention, the plurality of fluids can be guided to treat the operation target site with certainty. This will be described in more detail. As the laser light, carbon dioxide laser light, which is highly absorbable into water, is used. Therefore, even if the laser light leaks, the laser light is absorbed by water and thus the operation target site can be treated safely.

In addition, the fumes can be inhaled by the gap formation parts to treat the operation target site safely. This will be described in more detail. Carbon dioxide laser light, which is highly absorbable into water and highly absorbable into a surface of a living body, is used as the laser light in a bright visual field. Therefore, the operation target site can be irradiated with a minimum necessary amount of laser light and thus treated safely.

Effect of the Invention

According to the present invention, a laser treatment tool capable of guiding a plurality of fluids, a laser transmission path insertable into such a laser treatment tool, and an external tube for forming the laser transmission path can be provided.

BRIEF DESCRIPTION OF DRAWINGS

FIG. 3 provides isometric views illustrating a structure of an operation unit which can be operated by an operator (herein after, referred to simply as the "operation unit").

FIG. 4 provides isometric views illustrating a structure of a laser transmission path.

FIG. 5 provides cross-sectional views of the laser transmission path.

FIG. 6 provides cross-sectional views each illustrating a laser transmission path in another embodiment.

DESCRIPTION OF THE PREFERRED EMBODIMENTS

Hereinafter, an embodiment of the present invention will be described with reference to the drawings.

Figure 1:
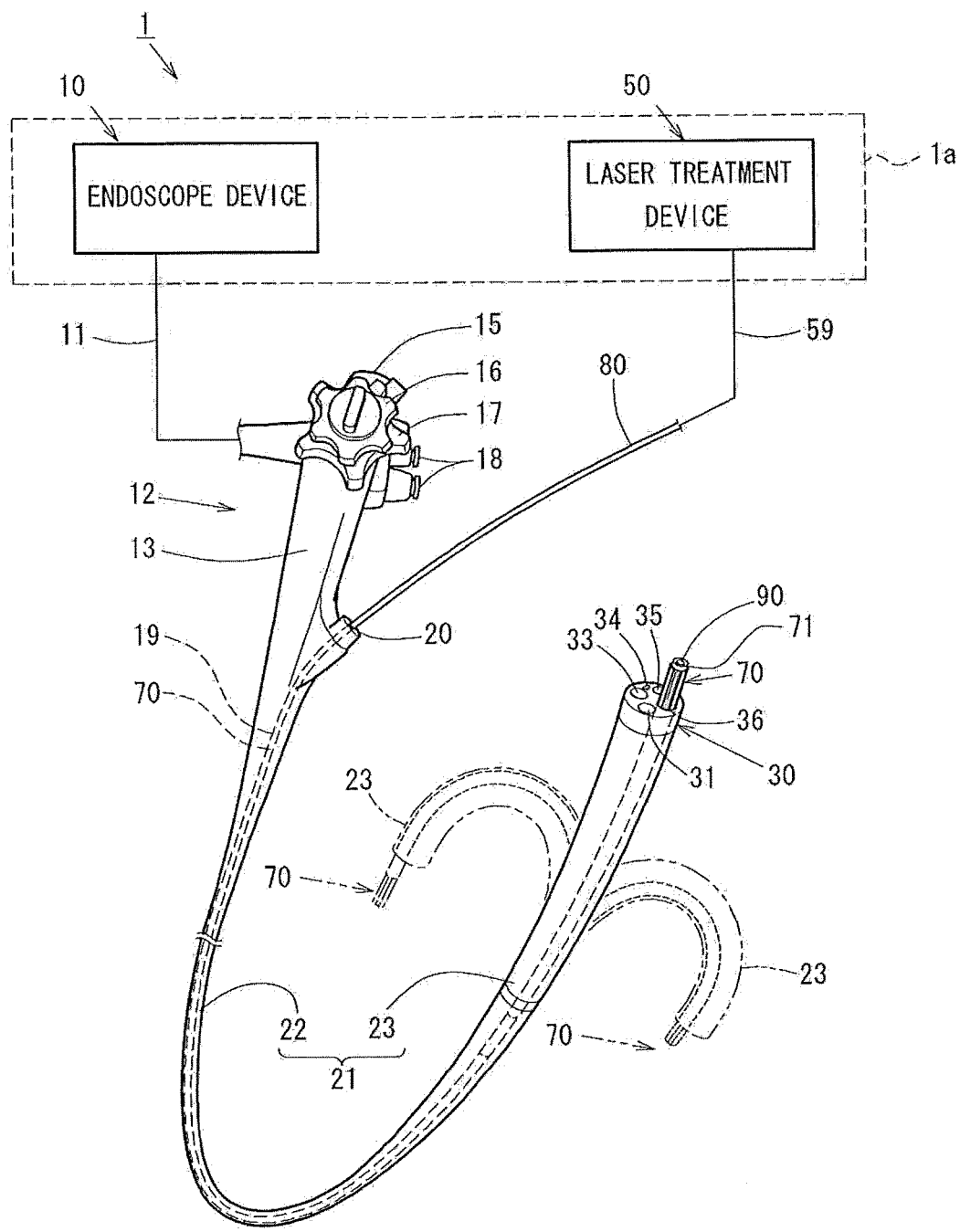
FIG. 1 is a schematic structural view of a laser treatment system including an endoscope device and a laser treatment device.
Figure 2:
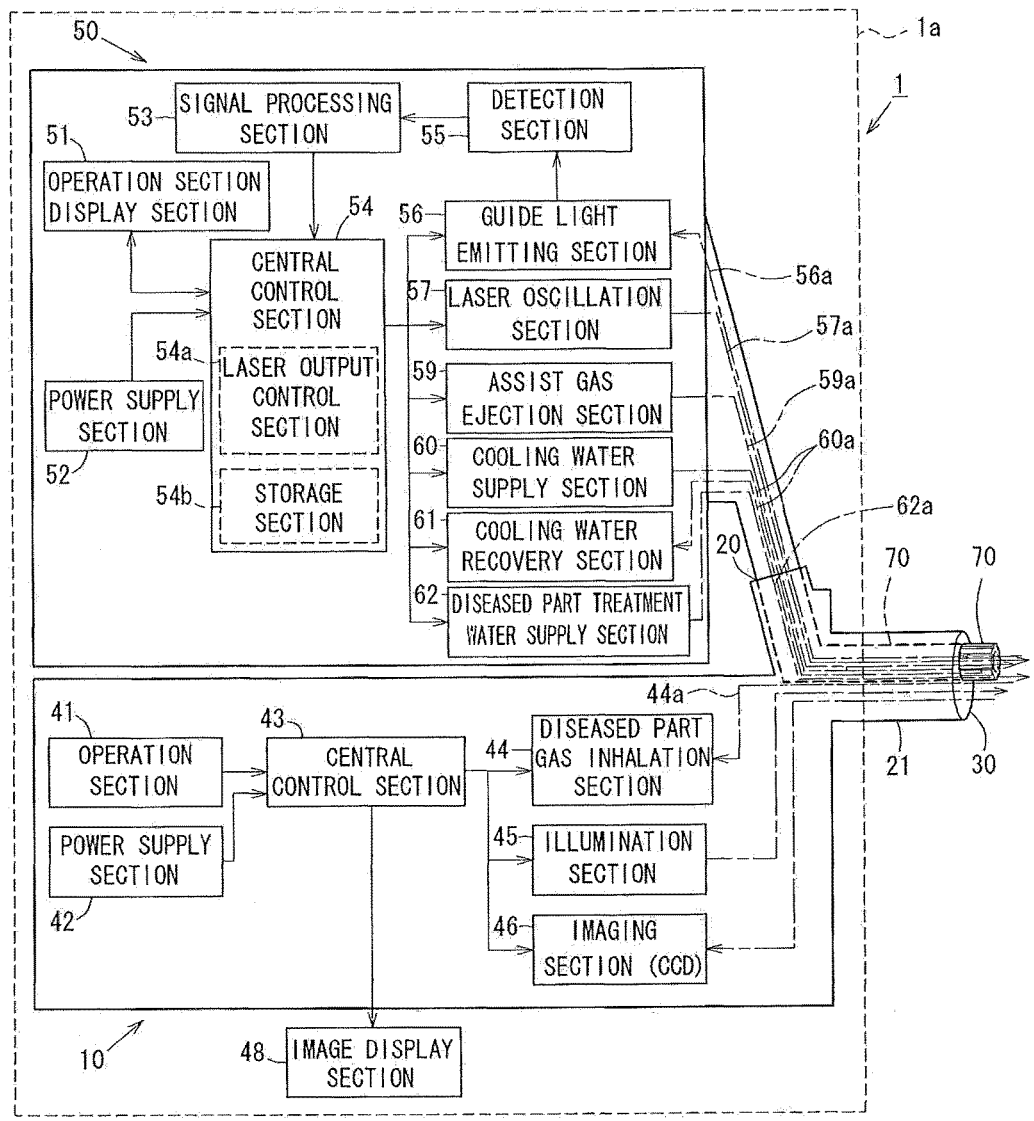
FIG. 2 is a block diagram showing a structure of the endoscope device and the laser treatment device.

FIG. 1 is a structural view schematically showing a structure of a laser treatment system 1 including an endoscope device 10 and a laser treatment device 50. FIG. 2 is a block diagram showing a structure of the endoscope device 10 and the laser treatment device 50.

As shown in FIG. 1, the endoscope device 10 is included in a device main body 1a and is connected to an operation unit 12 via a connection cable 11.

The operation unit 12 corresponding to a laser transmission tool mainly includes an operation section 13 and an endoscope tube 21.

The operation section 13 includes an eye contact section 15, an up-down angle knob 16, a left-right angle knob 17, operation buttons 18, a forceps insertion section 20, and the like.

The operation buttons 18 accept an operation input such as water supply, absorption, zooming, supply of assist gas described later, irrigation with diseased part treatment water, circulation of cooling water or the like.

The endoscope tube 21 corresponding to an endoscope external hose includes a flexible tube section 22, a curved tube section 23, and a tip structure section 30 provided in this order from a base part toward a tip thereof. The endoscope tube 21 has therein a forceps insertion path 19 corresponding to a transmission path insertion hole. The forceps insertion path 19 communicates from the forceps insertion opening 20 to a forceps exit 36 of the tip structure section 30, and acts as a treatment device insertion path, through which a treatment device such as forceps, a laser transmission path 70 or the like is insertable.

In FIG. 1, the endoscope tube 21 is shown as having a diameter increasing from the middle of the flexible tube section 22 toward a tip of the curved tube section 23. This is for easier understanding of the structure of the tip structure section 30, and in actuality, the endoscope tube 21 has a constant diameter suitable to allow a treatment device to be inserted into an organ in the body such as esophagus, stomach, the intestines or the like.

The flexible tube section 22 has a cylindrical shape which can be curved to an appropriate degree, and allows an appropriate treatment device, such as forceps or the like, inserted from the forceps insertion section 20 to reach the tip structure section 30. In this example, the laser transmission path 70 of the laser treatment device 50 is inserted and reaches the tip structure section 30 as the treatment device.

The curved tube section 23 is operable to be curved in an up-down direction by an operation on the up-down angle knob 16, and is operable to be curved in a left-right direction by an operation on the left-right angle knob 17.

This will be described in more detail. The curved tube section 23 is connected to the up-down angle knob 16 and the left-right angle knob 17 via a wire (not shown) inserted through the endoscope tube 21. Therefore, a rotation operation made on the up-down angle knob 16 or the left-right angle knob 17 is transmitted to the curved tube section 23 via the wire, and the curved tube section 23 is curved in the up-down direction or the left-right direction. Owing to this, the curved tube section 23 can be curved in an arbitrary direction at an arbitrary angle, and so the tip structure section 30 can be directed in an appropriate direction toward an operation target site.

The tip structure section 30 includes light guides 31 and 35, a lens 33, a nozzle 34, and the forceps exit 36.

The light guides 31 and 35 are illumination elements for providing light for illuminating a site to be imaged. Owing to this, a site in the body to which light does not reach is illuminated so that the operator can observe the site and performs a surgical operation on the site.

The lens 33 is a lens for collecting the light provided by, for example, the light guides 31 and 35 and reflected by the illuminated site in the body so as to obtain a shot image. By appropriately processing the collected information, a shot image is obtained and the operator can check the state of the site in the body. An imaging element for converting light into an electric signal may be provided in the vicinity of the tip structure section 30 and connected to the endoscope device 10 via a conductive wire, or may be provided inside the endoscope device 10 such that the light collected by the lens is transmitted by an image guide.

The nozzle 34 is an element for releasing, for example, a washing liquid for washing the lens 33 toward the lens 33.

The forceps exit 36 is an exit for a treatment device such as the laser transmission path 70 of the laser treatment device 50 or the like.

The laser transmission path 70 is formed to be longer than a length L1 of the forceps insertion path 19, which is the entire length of the endoscope tube 21. The laser transmission path 70 will be described in detail later.

As shown in FIG. 2, the laser treatment device 50 includes an operation section/display section 51, a power supply section 52, a signal processing section 53, a central control section 54 corresponding to a laser control section, a detection section 55, a guide light emitting section 56, a laser oscillation section 57 corresponding to a laser generation source, an assist gas ejection section 59, a cooling water supply section 60, a cooling water recovery section 61, and a diseased part treatment irrigation section 62.

The operation section/display section 51 accepts an operation input such as settings on laser output, change of an operation mode, or the like and transmits the input signal to the central control section 54. The operation section/display section 51 also receives a display signal on conditions of laser output, an operation state of the device or the like from the central control section 54 and displays appropriate information.

The power supply section 52 supplies operation electric power to the central control section 54 and other sections.

The signal processing section 53 processes the signal detected by the detection section 55 and transmits the signal to the central control section 54. In this example, the signal processing section 53 and the detection section 55 act together as an OCT (Optical Coherence Tomography) device.

The detection section 55 receives reflected guide light 55a (signal light), which is obtained by low coherence guide light 56a emitted from the guide light emitting section 56 being reflected by the operation target site, and reference light transmitted from the guide light emitting section 56, and thus obtains interfering light. Both of the lights received by the detection section 55 are near infrared light having a wavelength of 800 nm to 1 μm or in the vicinity thereof.

The detection section 55 detects light intensity of a be at signal generated by coherence of the reflected guide light 55a (signal light) and the reference light. The signal processing section 53 performs heterodyne detection of finding the intensity of the signal light reflected by a prescribed surface of the operation target site from the intensity of the light received from the detection section 55, and thus obtains optical coherence tomography information.

This is repeated while the operation target site to be detected is changed, and thus optical coherence tomography information of each of the operation target sites can be obtained. Owing to this, optical coherence tomography information including a tissue profile at a position having some depth from the surface is obtained. Namely, in addition to a tissue profile of a mucous membrane at the surface, a tissue profile of an area including a submucosal layer or a muscular layer is obtained. The optical coherence tomography information is information before the light is processed into an image. The signal processing section 53 transmits the optical coherence tomography information to the central control section 54.

The central control section 54 performs various control operations on various elements. The central control section 54 includes a laser output control section 54a and a storage section 54b.

The laser output control section 54a controls an output value of laser light 57a for treatment (herein after, referred to as the "treatment laser light 57a") which is output by the laser oscillation section 57, in accordance with the output set by the operation section/display section 51 or the operation mode.

The storage section 54b stores appropriate data in addition to control data on output setting, operation mode setting and the like.

As described above, the detection section 55 receives the reflected guide light 55a (signal light) and the reference light, and detects the light intensity of the be at signal generated from the interfering light.

The guide light emitting section 56 emits low coherence near infrared light having a wavelength of 800 nm to 1 μm or in the vicinity thereof. The guide light is provided for showing a position to be irradiated with the treatment laser light 57a. The near infrared light is invisible but can be detected by the imaging element and put into an image. Therefore, the near infrared light is converted into an image signal by an imaging section 46 of the endoscope device 10 described later and displayed on an image display section 48. Thus, the position to be irradiated with the treatment laser light 57a can be confirmed.

The laser oscillation section 57 oscillates the treatment laser light 57a to be used for the surgical operation. In this example, as the treatment laser light 57a, carbon dioxide laser light (herein after, referred to as the "$CO_2$ laser light") having a wavelength of 10.6 μm is used. Operations such as setting of the radiation strength of the $CO_2$ laser light, start and stop of the radiation and the like are performed by manual operations by use of the operation section/display section 51 and by the control of the central control section 54. A part of, or the entirety of, manual operations may be replaced with stomping operations using a foot controller (not shown) provided so as to be communicable with, and controllable with respect to, the laser treatment device 50.

The guide light 56a emitted by the guide light emitting section 56, the treatment laser light 57a oscillated by the laser oscillation section 57, and the reflected guide light 55a detected by the detection section 55 mentioned above are all transmitted by one hollow waveguide path 90. Accordingly, these types of light are all transmitted coaxially, and a site acting on the operation target and a site to be sensed match each other as the operation target site.

The assist gas ejection section 59 ejects carbon dioxide as assist gas 59a. It is desirable that the ejection pressure of the assist gas 59a, which passes through the laser transmission path 70 described later and is ejected toward the operation target site from a tip of the laser transmission path 70, is grasped by an appropriate pressure obtaining element.

The cooling water supply section 60 supplies cooling water 60a for cooling the hollow waveguide path 90 which has been heated by the treatment laser light 57a, and the cooling water recovery section 61 recovers the cooling water 60a which has cooled the hollow waveguide path 90. The cooling water 60a can be supplied by the cooling water supply section 60 and circulated after being recovered by the cooling water recovery section 61. The cooling water 60a may be fresh water instead of physiological saline solution.

The diseased part treatment irrigation section 62 may supply physiological saline solution as diseased part treatment water 62a in order to keep the diseased part bulged during the surgical operation.

The endoscope device 10 includes an operation section 41, a power source section 42, a central control section 43, a diseased part gas inhalation section 44 corresponding to a fluid inhalation unit, an illumination section 45, an imaging section 46, and the image display section 48.

The operation section 41 transmits an operation input made by the operation section 13 (see FIG. 1) to the central control section 43. Namely, the operation section 41 transmits a curving operation on the curved tube section 23 made by an operation on the up-down angle knob 16 or the left-right angle knob 17, a pressing operation made by the operation buttons 18, or the like. Alternatively, an operation section is provided in, for example, a control device main body (not shown) of the endoscope device, separately from the operation section 41 of the operation unit 12, and an operation on the illumination light amount, imaging and storage of a still image or the like is transmitted to the central control section 43.

The power supply section 42 supplies operation electric power to the central control section 43 and other sections.

The central control section 43 performs various control operations on various elements.

The diseased part gas inhalation section 44 inhales diseased part gas 44a which is filling the diseased part via inhalation guide paths 19b each corresponding to a fluid absorption passage which is formed between the laser transmission path 70 described later and the forceps insertion path 19 of the endoscope tube 21.

The illumination section 45 provides illumination light from the light guides 31 and 35 (see FIG. 1).

The imaging section 46 shoots an image transmitted from the lens 33 (see FIG. 1) and thus obtains an image necessary for the surgical operation. Images necessary for the surgical operation are obtained in real time continuously, so that the operator can performs the surgical operation smoothly.

The image display section 48 displays images based on the signal transmitted from the central control section 43. Such images include the shot image obtained by the imaging section 46. Accordingly, the operator can perform the surgical operation while checking the shot image displayed on the image display section 48 in real time. A pre-operation image may be stored, for example, in the central control section 43, on a communicable external storage device or the like as a still image, and may be retrieved and displayed after the surgical operation and compared with a post-operation image.

Now, the laser transmission path 70 will be described with reference to FIG. 3 through FIG. 5. FIG. 3 provides isometric views illustrating a structure of the operation unit 12. In more detail, FIG. 3(*a*) is an isometric view of the curved tube section 23, and FIG. 3(*b*) is an enlarged view of part "a" in FIG. 3(*a*).

FIG. 4 provides isometric views illustrating a structure of the laser transmission path 70. FIG. 4(*a*) is an isometric view of the laser transmission path 70 in which an external tube 80 and a tip ejection outlet member 71 are shown as being partially cut away, and FIG. 4(*b*) is an isometric view of the external tube 80. FIG. 4(*c*) is an isometric view of the tip ejection outlet member 71, and FIG. 4(*d*) is an isometric view of the hollow waveguide path 90. FIG. 4(*e*) is an isometric view of the tip ejection outlet member 71 in the state where the hollow waveguide path 90 is inserted thereinto.

In FIG. 4(*b*), a tip insertion part 80a of the external tube 80 into which the tip ejection outlet member 71 is insertable is shown as being transparent. In FIG. 4(*e*), the tip ejection outlet member 71 is shown as being partially cut away, and the hollow waveguide path 90 is shown as being transparent.

FIG. 5 provides cross-sectional views illustrating the laser transmission path 70. FIG. 5(*a*) is a vertical cross-sectional view of FIG. 5(*b*) taken along line C-C, of the laser transmission path 70 inserted into the forceps insertion path 19 of the endoscope tube 21. FIG. 5(*b*) is a cross-sectional view of FIG. 5(*a*) taken along line A-A and seen in the direction of the arrows of line A-A. FIG. 5(*c*) is a cross-sectional view of FIG. 5(*a*) taken along line B-B and seen in the direction of the arrows of line B-B.

The laser transmission path 70 includes the external tube 80, the tip ejection outlet member 71, and the hollow waveguide path 90. As described above, the laser transmission path 70 is formed to be longer than the endoscope tube 21.

The external tube 80 is a hollow flexible resin tube having an insertion space 81 corresponding to an insertion hole therein. The external tube 80 has a diameter approximately equal to an inner diameter of the forceps insertion path 19 of the endoscope tube 21. The external tube 80 includes outer circumferential convexed parts 82 corresponding to projections and outer circumferential concaved parts 83 corresponding to concaved parts or gap formation parts. The outer circumferential concaved parts 83 are each provided between adjacent circumferential convexed parts 82 and are recessed with respect to the circumferential convexed parts 82. The circumferential convexed parts 82 and the outer circumferential concaved parts 83 are located side by side in a circumferential direction of the external tube 80, so that the external tube 80 is generally gear-like when seen in a front cross-sectional view as shown in FIG. 5(*b*) and FIG. 5(*c*). In the state where the external tube 80 is inserted into the endoscope tube 21, a gap between each of the outer concaved parts 83 and an inner circumferential surface 19a of the forceps insertion path 19 acts as the inhalation guide path 19b.

As described above, the inhalation guide paths 19b are each communicated to the diseased part gas inhalation section 44 of the endoscope device 10. The above-mentioned diseased part gas 44a is inhaled by the diseased part gas inhalation section 44 via the inhalation guide paths 19b.

At a tip of the insertion space 81 of the external tube 80, the tip insertion part 80a for allowing insertion of the tip ejection outlet member 71 described later is formed.

A part of the insertion space 81 of the external tube 80 other than the tip insertion part 80a accommodates sub passages 84 (84a, 84b and 84c) corresponding to fluid passages. As shown in the cross-section in FIG. 5(*c*), the sub passages 84 (84a, 84b and 84c) are formed at three different positions along the circumferential direction of the external tube 80. The sub passages 84 (84a, 84b and 84c) are formed on an inner circumferential surface of the external tube 80 and extend in a longitudinal direction thereof.

The sub passages 84 are sized such that inner tips thereof in the cross-sectional view shown in FIG. 5(*c*) define a circle which is larger by a certain degree than an outer diameter of the hollow waveguide path 90 inserted into the insertion space 81.

The tip ejection outlet member 71 is a generally cylindrical member which can be pressurized into the tip insertion section 80a at a tip of the external tube 80. The tip ejection outlet member 71 includes a front cylindrical part 71a on a front side (diseased part side) thereof in an axial direction, namely, in a longitudinal direction thereof, and a rear cylindrical part 71b on a rear side thereof.

The tip ejection outlet member 71 has a central radiation hole 72 at a center thereof as seen in a front view. The central radiation hole 72 runs throughout the tip ejection outlet member 71 in the axial direction, namely, in the longitudinal direction thereof. Also as seen in the front view, the tip ejection outlet member 71 has an assist gas ejection hole 73, an irrigation hole 74, and a cooling water circulation path 75 at three positions which are radially outer to the central radiation hole 72. The three positions correspond to the positions of the sub passages 84.

The central radiation hole 72 includes a front radiation hole 72a formed in the front cylindrical part 71a and a rear radiation hole 72b formed in the rear cylindrical part 71b (see FIG. 4(*e*)). The front radiation hole 72a has a diameter which is approximately equal to the outer diameter of the hollow waveguide path 90 and allows insertion of the hollow waveguide path 90. The rear radiation hole 72b has a diameter which is larger by a certain degree than the outer diameter of the hollow waveguide path 90 and has a gap around the hollow waveguide path 90 inserted thereinto.

The assist gas ejection hole 73 and the irrigation hole 74 run throughout the tip ejection outlet member 71 in the axial direction, namely, in the longitudinal direction thereof.

By contrast, the cooling water circulation path 75 runs forward from the rear side of the tip ejection outlet member 71 and is bent to be communicated to the front side of the rear irradiation hole 72*b*. Namely, the cooling water circulation path 75 is a through-hole running through the rear cylindrical part 71*b* from the rear side of the tip ejection outlet member 71 to the front side of the rear irradiation part 72*b*. Therefore, the assist gas ejection hole 73 is in communication with the assist gas sub passage 84*a* corresponding to an assist gas passage, the irrigation hole 74 is in communication with the diseased part treatment water sub passage 84*b* corresponding to an irrigation passage, and the cooing water circulation path 75 is in communication with the cooling water recovery sub passage 84*c*.

As shown in the vertical cross-sectional view of FIG. 5(*a*), the hollow waveguide path 90 is a cylindrical member having a tip part which is insertable into the front irradiation hole 72*a* of the central irradiation hole 72 and having the outer diameter which is equal to an inner diameter of the front irradiation hole 72*a*. The inner circumferential surface of the hollow cylindrical member is entirely covered with a dielectric thin film 91. The cylindrical member used to form the hollow waveguide path 90 is formed to be lengthy, and is formed of glass or the like, namely, a material which has a smooth surface and is suitable for forming a reflective film of silver or the like and a dielectric thin film. The dielectric thin film 91 is formed of an appropriate material capable of reflecting and transmitting laser light highly efficiently, for example, COP (cyclic olefin polymer), polyimide or the like.

Since the inner circumferential surface of the hollow waveguide path 90 is covered with a reflective film of silver or the like and the dielectric film 91 as described above, the treatment laser light 57*a*, the guide light 56*a* or the reflected guide light 55*a*, guided through the guide space 92 in the hollow waveguide path 90, can be guided at high transmission efficiency.

As described above, the hollow waveguide path 90 is formed of a cylindrical member having the outer diameter equal to the inner diameter of the front irradiation hole 72*a* of the central irradiation hole 72. Therefore, cooling water passages 85 corresponding to the fluid passage or the cooling water passage are formed between an inner circumferential surface 80*b* of the external tube 80 and an outer circumferential surface 90*a* of the hollow waveguide path 90.

This will be described in more detail. The cooling water passages 85 formed between the outer circumferential surface 90*a* of the hollow waveguide path 90 and the inner circumferential surface 80*b* of the external tube 80 are in communication with the gap formed between the rear irradiation hole 72*b* of the central irradiation hole 72 and the outer circumferential surface 90*a* of the hollow waveguide path 90. The cooling water passages 85 are in communication with the cooling water recovery sub passage 84*c* corresponding to a cooling water recovery passage via the gap formed between the rear irradiation hole 72*b* of the central irradiation hole 72 and the outer circumferential surface 90*a* of the hollow waveguide path 90 and the cooling water circulation path 75.

A base part of the assist gas sub passage 84*a* is connected to the assist gas ejection section 59 of the laser treatment device 50. Accordingly, the assist gas 59*a* ejected by the assist gas ejection section 59 is guided from the base part to a tip part of the assist gas sub passage 84*a*, and can be ejected forward from the assist gas ejection hole 73 of the tip ejection outlet member 71.

A base part of the diseased part treatment water sub passage 84*b* is connected to the diseased part treatment irrigation section 62 of the laser treatment device 50. Accordingly, the diseased part treatment water 62*a* supplied by the diseased part treatment irrigation section 62 is guided from the base part to a tip part of the diseased part treatment water sub passage 84*b*, and can be released forward from the irrigation hole 74 of the tip ejection outlet member 71.

Base parts of the cooling water passages 85 are connected to the cooling water supply section 60 of the laser treatment device 50, and a base part of the cooling water recovery sub passage 84*c* is connected to the cooling water recovery section 61 of the laser treatment device 50. Accordingly, the cooling water 60*a* supplied by the cooling water supply section 60 is guided from the base parts to tip parts of the cooling water passages 85, passes the cooling water circulation path 75, is guided rearward in the cooling water recovery sub passage 84*c*, and can be recovered by the cooling water recovery section 61.

Now, a method for using the laser treatment system 1 in the endoscopic submucosal dissection (ESD) will be described.

As described above, in the endoscopic submucosal dissection (ESD) using the laser treatment system 1, the operation unit 12 having the laser transmission path 70 inserted into the forceps insertion path 19 is inserted into the body. Based on an image of an area forward to the tip structure section 30 shot by the imaging section 46 and displayed on the image display section 48, the tip structure section 30 of the operation unit 12 is inserted until reaching the operation target site. The operation target site is a tubular cavity such as esophagus, stomach or the like, namely, an appropriate site in a living organism such as a human or the like.

Then, the assist gas ejection section 59 is activated to eject the assist gas 59*a* via the assist gas sub passage 84*a* and the assist gas ejection hole 73 of the tip ejection outlet member 71. Thus, the tubular cavity as the operation target site is inflated into a state where the surgical operation can be performed easily.

The diseased part treatment irrigation section 62 is activated to release the diseased part treatment water 62*a* via the diseased part treatment water sub passage 84*b* and the irrigation hole 74 of the tip ejection outlet member 71. Thus, the operation target site is bulged into a state where the surgical operation can be performed easily.

The operator performs a treatment on the operation target site by use of the treatment laser light 57*a*, while checking the image on the image display section 48 and also while providing the guide light 56*a* and the treatment laser light 57*a*, which are guided through the guide space 92 of the hollow waveguide path 90, from the central radiation hole 72 of the tip ejection outlet member 71.

Since the operation target site is incised and ablated by use of the treatment laser light 57*a*, the tubular cavity as the operation target site is filled with fumes. However, the assist gas 59*a* is ejected and the diseased part gas inhalation section 44 is activated, so that the diseased part gas 44*a* containing the fumes in the tubular cavity can be absorbed by the diseased part gas inhalation section 44 via the inhalation guide paths 19*b*. Therefore, the tubular cavity as the operation target site can be kept clear.

The cooling water supply section 60 and the cooling water recovery section 61 are activated to circulate the cooling water 60a via the cooling water passages 85, the cooling water circulation path 75 and the cooling water recovery sub passage 84c. Thus, the hollow waveguide path 90, which has been heated by the treatment laser light 57a, can be cooled by the cooling water 60a. The cooling water passages 85 are structured to be in contact with the outer circumferential surface of the hollow waveguide path 90 in a heated state, and therefore the hollow waveguide path 90 can be efficiently cooled by the cooling water 60a.

As the treatment laser light 57a, $CO_2$ laser light, which is highly absorbable into water, is used, and the cooling water 60a is supplied to the cooling water passages 85 around the hollow waveguide path 90. Therefore, even if the hollow waveguide path 90 is broken and the treatment laser light 57a guided through the guide space 92 leaks (erroneous radiation), the external tube 80 and the endoscope tube 21 of the operation unit 12 are prevented from being damaged by such erroneous radiation of the treatment laser light 57a. Therefore, the operation unit 12 can provide high safety and high reliability.

The cooling water 60a is supplied from the cooling water supply section 60 and is recovered to the cooling water recovery section 61 via the cooling water passages 85, the cooling water circulation path 75 and the cooling water recovery sub passage 84c. Namely, the cooling water 60a circulates without leaking outside. Thus, the cooling water 60a does not need to be physiological saline solution and may be fresh water.

After the surgical operation is completed, the operation unit 12 is extracted from the body, and thus the endoscopic submucosal dissection (ESD) is completed. The laser treatment system 1 can be used in substantially the same manner for the endoscopic mucosal resection (EMR).

As described above, the external tube 80 forms the laser transmission path 70 together with the lengthy hollow waveguide path 90 for guiding the treatment laser light 57a and allows the hollow waveguide path 90 to be inserted into the inner insertion space 81 thereof. The external tube 80 includes the plurality of sub passages 84 and cooling water passages 85 located outside the hollow waveguide path 90, inserted into the insertion space 81, along the longitudinal direction of the insertion space 81. Thus, the laser transmission path 70 is formed by use of the external tube 80. Owing to this, the laser transmission path 70 can guide a plurality of fluids (cooling water, assist gas, diseased part treatment water, diseased part gas, etc.).

This will be described in more detail. The plurality of sub passages 84 and cooling water passages 85 are provided outside the hollow waveguide path 90 along the longitudinal direction of the insertion space 81. Owing to this, appropriate fluids are guided through the plurality of passages, for example, the cooling water passages 85 for the cooling water 60a, the cooling water recovery sub passage 84c for recovering the cooling water 60a, and the like. Thus, a plurality of desired fluids can be guided.

The plurality sub passages 84 are located between the hollow waveguide path 90 inserted into the insertion space 81 and an inner surface of the insertion space 81, at an equal interval with respect to the inner surface. Owing to this, the hollow waveguide path 90 inserted into the insertion space 81 inside the external tube 80 can be positioned at the center of the external tube 80 with certainty, and a space enclosed by the plurality of sub passages 84 located at an equal interval and an outer circumferential surface of the hollow waveguide path 90 can act as the cooling water passages 85.

The external tube 80 is inserted into the forceps insertion path 19 of the endoscope tube 21. The external tube 80 further includes the outer circumferential convexed parts 82 located at least at two positions as seen in a cross-section of the external tube 80 and projecting outward in a radial direction such that in the state where the external tube 80 is inserted into the forceps insertion path 19, tips of the outer circumferential convexed parts 82 are in contact with the inner circumferential surface of the forceps insertion path 19; and the outer circumferential concaved parts 83 for forming gaps together with the inner surface of the forceps insertion path 19, the gaps being formed between adjacent outer circumferential convexed parts 82. The laser transmission path 70 is formed by use of the external tube 80, and the laser transmission path 70 formed by use of the external tube 80 is inserted into the forceps insertion path 19 of the endoscope tube 21 included in the operation tool 12. Owing to this, the fumes are inhaled by the inhalation guide paths 19b formed by the outer circumferential concaved parts 83. Thus, in a cauterization operation performed by use of the treatment laser light 57a, especially in endoscopic submucosal dissection (ESD) or endoscopic mucosal resection (EMR), the operation target site can be expanded and also the visual field can be securely obtained. Therefore, reliable and safe surgical operations can be performed.

The laser transmission path 70 formed by use of the external tube 80 is inserted into the forceps insertion path 19 of the endoscope tube 21 included in the operation unit 12. Owing to this, the laser transmission path 70 can be positioned at the center of the forceps insertion path 19.

The external tube 80 includes the plurality of outer circumferential convexed parts 82 and outer circumferential concaved parts 83 located continuously in the circumferential direction of the external tube 80 so as to have a gear-like cross-section. Owing to this, the laser transmission path 70 formed by use of the external tube 80 can be positioned at the center of the forceps insertion path 19 with more certainty. In addition, the fumes can be absorbed by the inhalation guide paths 19b formed by the outer circumferential concaved parts 83 provided in the circumferential direction.

The laser transmission path 70 includes the hollow waveguide path 90 inserted into the insertion space 81 of the above-described external tube 80. In the laser transmission path 70, the plurality of fluids can be guided to treat the operation target site with the treatment laser light 57a with certainty.

This will be described in more detail. The hollow waveguide path 90 is inserted into the insertion space 81 of the external tube 80. Thus, the plurality of sub passages 84 and cooling water passages 85 are provided outside the hollow waveguide path 90 along the longitudinal direction of the insertion space 81. Owing to this, appropriate fluids are guided through the plurality of passages, for example, the cooling water passages 85 for the cooling water 60a, the cooling water recovery sub passage 84c for recovering the cooling water 60a, and the like. Thus, while a plurality of desired fluids are guided, the operation target site can be treated with the treatment laser light 57a with certainty.

The cooling water 60a for cooling the hollow waveguide path 90 is supplied to the cooling water passages 85 such that the cooling water 60a flows in a direction in which the treatment laser light 57a is directed. Owing to this, the hollow waveguide path 90 which has been heated by the treatment laser light 57a can be cooled by the cooling water 60a flowing in the fluid passage. Therefore, the laser transmission path 70 for providing the treatment laser light 57*a* for treating the operation target site with certainty can be improved in durability.

In the cooling water recovery sub passage 84*c* among the plurality of sub passages 84, the cooling water 60*a* which has cooled the hollow waveguide path 90 is allowed to flow in a direction opposite to the direction in which the treatment laser light 57*a* is directed. Thus, the cooling water 60*a* is recovered. In this manner, the cooling water 60*a* can be circulated, and the hollow waveguide path 90 which has been heated by the treatment laser light 57*a* can be cooled efficiently.

To the diseased part treatment water sub passage 84*b* among the plurality of sub passages 84, the diseased part treatment water 62*a* is supplied such that diseased part treatment water 62*a* flows in the direction in which the treatment laser light 57*a* is directed and is released toward the diseased part. Therefore, while the hollow waveguide path 90 which has been heated is cooled by the cooling water 60*a*, the diseased part treatment water 62*a* is released toward the operation target site (diseased part) in the body such as the wall of esophagus, the wall of stomach or the like. Owing to this, for example, while the operation target site (diseased part) is bulged or the like to, for example, securely obtain the visual field, the operation target site can be treated with the treatment laser light 57*a* with certainty.

To the assist gas sub passage 84*a* among the plurality of sub passages 84, the assist gas 59*a* is supplied such that the assist gas 59*a* flows in the direction in which the treatment laser light 57*a* is directed and is released toward the diseased part. Therefore, while the hollow waveguide path 90 which has been heated is cooled by the cooling water 60*a*, the assist gas 59*a* is guided and is ejected toward the operation target site in the body such as the wall of esophagus, the wall of stomach or the like. Owing to this, while the treatment space is expanded and also the fumes are removed to, for example, securely obtain the visual field, the operation target site can be treated with the treatment laser light 57*a* with certainty.

In the above description, carbon dioxide, which is more absorbable in the body than air, is used as the assist gas 59*a*. Therefore, the following advantage is provided. The treatment laser light 57*a* is guided through the hollow waveguide path 90, and the assist gas 59*a* is guided through the assist gas sub passage 84*a* which is outside the hollow waveguide path 90 and inside the external tube 80. Namely, the treatment laser light 57*a* and the assist gas 59*a* are guided through separate guide paths. Therefore, an inconvenience which would occur in the case where the treatment laser light 57*a* and the assist gas 59*a* are guided through the same guide path, namely, the inconvenience that the treatment laser light 57*a* is absorbed by the assist gas 59*a* and as a result, the operation target site cannot be irradiated with the treatment laser light 57*a* of a desired output, does not occur. Thus, reduction of the transmission efficiency of the treatment laser light 57*a* which would be caused by such an inconvenience can be prevented. The treatment laser light 57*a* and the assist gas 59*a* are guided without the transmission efficiency of the treatment laser light 57*a* being reduced, and the assist gas 59*a* is ejected toward the operation target site in the body such as the wall of esophagus, the wall of stomach or the like. Owing to this, while the treatment space is expanded and also the fumes are removed to, for example, securely obtain the visual field, the operation target site can be treated with the treatment laser light 57*a* with certainty.

In other words, the freedom degree of combination of the assist gas 59*a* and the treatment laser light 57*a* is increased. As a result, the convenience is improved.

The laser transmission path 70 includes the hollow waveguide path 90 inserted into the insertion space 81 of the external tube 80. In the laser transmission path 70, the fumes are inhaled by the inhalation guide paths 19*b* formed by the outer circumferential concaved parts 83, and thus the operation target site can be treated with the treatment laser light 57*a* with certainty.

The operation unit 12 includes the laser oscillation section 57, the central control section 54, and the laser transmission path 70. The laser transmission path 70 is inserted into the forceps insertion path 19 of the endoscope tube 21, and the tip of the laser transmission path 70 is located in the vicinity of the tip opening of the endoscope tube 21. Therefore, the tip of the laser transmission path 70 for providing the treatment laser light 57*a* can be guided to the operation target site with certainty.

This will be described in more detail. Usually, the endoscope tube 21 includes a plurality of channels, and one of the channels includes an image fiber. The image fiber has the imaging section 46 at an end thereof on the side of a main body. Alternatively, the image fiber has the imaging section 46 at a tip of the channel on the side of a diseased part. Therefore, the operator can allow the tip of the endoscope tube 21 to reach the operation target site while checking an image shot by the imaging section 46. Hence, the tip of the laser transmission path 70 inserted into the endoscope tube 21 and located in the vicinity of the tip opening of the endoscope tube 21 can be guided to a position very close to the operation target site with certainty. Therefore, the assist gas 59*a* can be ejected toward the operation target site in the body such as the wall of esophagus, the wall of stomach or the like. Thus, the treatment space is expanded and also the fumes are removed to, for example, securely obtain the visual field, and also the operation target site can be treated with the treatment laser light 57*a* with more certainty.

The operation unit 12 includes the laser oscillation section 57, the central control section 54, and the laser transmission path 70. The laser transmission path 70 is inserted into the forceps insertion path 19 of the endoscope tube 21 such that the tip of the laser transmission path 70 is located in the vicinity of the tip opening of the endoscope tube 21; and the diseased part gas inhalation section 44 is connected to the outer circumferential concaved parts 83, and the inhalation guide paths 19*b* are formed by the outer circumferential concaved parts 83. Owing to this, the tip of the laser transmission path 70 for providing the treatment laser light 57*a* can be guided to the operation target site with certainty.

As the treatment laser light 57*a*, carbon dioxide laser light ($CO_2$ gas laser light) is used. Therefore, the plurality of fluids can be guided to treat the operation target site with certainty. This will be described in more detail. As the treatment laser light 57*a*, carbon dioxide laser light ($CO_2$ gas laser light), which is highly absorbable into water, is used. Therefore, even if the treatment laser light 57*a* leaks, the treatment laser light 57*a* is absorbed by water and thus the operation target site can be treated safely.

In addition, since the treatment laser light 57*a* is carbon dioxide laser light ($CO_2$ gas laser light), the fumes can be inhaled by the outer circumferential concaved parts 83 to treat the operation target site safely. This will be described in more detail. Carbon dioxide laser light ($CO_2$ gas laser light), which is highly absorbable into water and highly absorbable into a surface of a living body, is used as the treatment laser light 57*a* in a bright visual field. Therefore, the operation target site can be irradiated with a minimum necessary amount of laser light and thus treated safely.

$CO_2$ gas, which is bioabsorbable, is used as the assist gas 59a. Therefore, the assist gas 59a filling the operation target site after the surgical operation can be rapidly absorbed, and thus a sensation of distention or pain after the surgical operation can be suppressed. Even if the assist gas 59a enters a blood vessel, there is no risk of air embolism of the blood vessel because the assist gas 59a is bioabsorbable.

As described above, the treatment laser light 57a is guided through the hollow waveguide path 90, and the assist gas 59a is guided through the assist gas sub passage 84a and the assist gas ejection hole 73 of the tip ejection outlet member 71. Owing to this, the assist gas 59a is ejected toward the operation target site in the body such as the wall of esophagus, the wall of stomach or the like. Thus, while the treatment space is expanded and also the fumes are removed to, for example, securely obtain the visual field, the operation target site can be treated with the treatment laser light 57a with certainty.

The operation unit 12 may include a plurality of forceps insertion paths 19. In this operation unit 12, the laser transmission path 70 is inserted into one of the forceps insertion paths 19, and the tip of the laser transmission path 70 is located in the tip structure section 30 of the endoscope tube 21. The operation unit 12 also includes an optical system including the illumination section 45 apart from the forceps insertion paths 19. Therefore, while the image obtained by the illumination section 45 is checked, the tip structure section 30 of the endoscope tube 21 of the operation unit 12 can be guided to a position very close to the operation target site.

Accordingly, the assist gas 59a is ejected toward the operation target site in the body such as the wall of esophagus, the wall of stomach or the like. Thus, the treatment space is expanded and also the fumes are removed to, for example, securely obtain the visual field, and also the operation target site can be treated with the treatment laser light 57a with certainty while the shot image is checked.

In the above description, the external tube 80 includes the outer circumferential convexed parts 82 and the outer circumferential concaved parts 83 to have a gear-like cross-section, and also includes the sub passages 84 at three positions in the insertion space 81 as seen in a cross-sectional view thereof. The laser transmission path 70 formed by use of the external tube 80 is inserted into the forceps insertion path 19 of the endoscope tube 21. The inhalation guide paths 19b are formed between the inner surface of the forceps insertion path 19 and the outer circumferential convexed parts 82, and the cooling water passages 85 are formed between the outer circumferential surface of the hollow waveguide path 90 and the inner circumferential surface of the external tube 80. Alternatively, as shown in FIG. 6, the laser transmission path 70 may be formed by use of an external tube having another shape.

For example, an external tube 180 shown in FIG. 6(a) has a generally triangular shape as seen in a front cross-section. The triangular shape is formed of three convexed apexes 182 and sides 183 located there between. The sides 183 are recessed with respect to the apexes 182 in a radial direction. As seen in the front cross-section, the external tube 180 includes the insertion space 81 at a center thereof, and also includes sub passages 184 (184a, 184b, 184c) respectively in the vicinity of the apexes 182.

The insertion space 81 is formed to have a diameter larger by a certain degree than the hollow waveguide path 90 to be inserted therethrough, and forms a cooling water passage 185 around the hollow waveguide path 90 inserted therethrough.

The apexes 182 are in contact with the inner circumferential surface 19a of the forceps insertion path 19 of the endoscope tube 21, and form the inhalation guide paths 19b between an inner circumferential surface of the forceps insertion path 19 and the sides 183.

An external tube 280 shown in FIG. 6(b) has a generally gear-like shape as seen in a front cross-section. The generally gear-like shape is formed of the outer circumferential convexed parts 82 and the inner circumferential concaved parts 83. As seen in the front cross-section, the external tube 280 includes the insertion space 81 at a center thereof. A passage outer to the insertion space 81 is equally divided into three in the circumferential direction of the insertion space 81 and thus sub passages 284 (284a, 284b, 284c) are formed.

An external tube 380 shown in FIG. 6(c) has an elliptical shape as seen in a front cross-section. The elliptical cross-section is longer in the up-down direction in FIG. 6(c). Arcked parts 382 at both ends of the longer axis of the elliptical cross-section contact the inner circumferential surface 19a of the forceps insertion hole 19, and the inhalation guide paths 19b are formed between arcked parts 383 at both ends of the shorter axis of the elliptical cross-section and the inner circumferential surface 19a of the forceps insertion hole 19.

As seen in the front cross-section, the external tube 380 includes the insertion space 81 at a center thereof, and also includes sub passages 384 (384a, 384c) inside the arcked parts 383 on at both of ends of the shorter axis. Cooling water passages 385 are formed around the hollow waveguide path 90 inserted into the insertion space 81.

Owing to such structures, the external tubes 180, 280 and 380 shown in FIG. 6(a) through FIG. 6(c) also provide substantially the same effects as those of the external tube 80 described above.

In the above description, carbon dioxide laser light ($CO_2$ gas laser light) is used as the treatment laser light 57a. Alternatively, any other appropriate treatment laser light may be used.

In the curved tube section 23, the hollow waveguide path 90 may be inserted into a protective metal tube, so that the hollow waveguide path 90 is surrounded by the protective metal tube. Owing to this, the operator can allow the curved tube section 23 to be freely curved to perform a laser treatment highly safely and highly reliably in a favorable work environment.

The laser treatment device 50 may include an SAG ejection section for ejecting an appropriate gas which is not light absorbable or bioabsorbable such as air or the like as sub assist gas (herein after, referred to as the "SAG"). With such a structure, the treatment laser light 57a and the SAG may be directed and ejected from the central irradiation hole 72 of the tip ejection outlet member 71 to treat the operation target site with the treatment laser light 57a. In this case, both of the treatment laser light 57a and the SAG are ejected toward the guide space 92 of the hollow waveguide path 90. Therefore, transpired substances generated by the incision and ablation of the operation target site performed by use of the treatment laser light 57a are prevented from entering the central irradiation hole 72 or the guide space 92.

As the SAG, air, which is less bioabsorbable than $CO_2$ gas used as the assist gas 59a is used. However, the SAG is absorbed with certainty by the outer circumferential concaved parts; and in addition, the SAG puts the guide space 92 of the hollow waveguide path 90 into a positive pressure, and is ejected at an amount and a pressure at which invasion of transpired substances to the central radiation hole 72 of the laser transmission path 70 is prevented. Therefore, the use of air as the SAG does not influence the occurrence of a sensation of distention or pain after the surgical operation. In addition, the SAG is ejected at the above-described amount and pressure, and therefore there is no risk of air embolism of a blood vessel being caused by the air entering the blood vessel and air bubbles staying therein. Hence, the use of air as the SAG is safe.

The laser light according to the present invention corresponds to the treatment laser light 57a in the above-described embodiment; and in the same manner, the endoscope external hose corresponds to the endoscope tube 21;

the transmission path insertion hole corresponds to the forceps insertion path 19:

the insertion hole corresponds to the insertion space 81;

the fluid passages correspond to the sub passages 84, 184, 284 and 384, the assist gas sub passages 84a, 184a, 284a and 384a, the diseased part treatment water sub passages 84b, 184b and 284b, the cooling water recovery sub passages 84c, 184c, 284c and 384c, and the cooling water passages 85, 185, 285 and 385;

the inner surface of the transmission path insertion hole corresponds to the inner circumferential surface 19a;

the projections correspond to the outer circumferential convexes parts 82, the apexes 182, and the arced parts 382 at both ends of the longer axis;

the convexed parts correspond to the outer circumferential concaved parts 83, the sides 183, and the arced parts 383 at both ends of the shorter axis;

the cooling water passage corresponds to the cooling water passage 85;

the cooling water recovery passage corresponds to the cooling water recovery sub passage 84c;

the irrigation passage corresponds to the diseased part treatment water sub passage 84b;

the assist gas passage corresponds to the assist gas sub passage 84a;

the laser generation source corresponds to the laser oscillation section 57;

the laser control section corresponds to the central control section 54;

the fluid inhalation unit corresponds to the diseased part gas inhalation section 44;

the fluid absorption passages correspond to the inhalation guide paths 19b; and the laser treatment tool corresponds to the operation unit 12.

However, the present invention is not limited to the above-described embodiment, and can be carried out in many other embodiments.

For example, the ejection amount or the ejection pressure of the assist gas 59a may be both detected, and the laser treatment system 1 may be deactivated when an abnormal value is detected. In more detail, by detecting the ejection amount or the ejection pressure of the assist gas 59a independently or relatively, it can be detected whether the assist gas sub passage 84a or the assist gas ejection hole 73 through which the assist gas 59a passes is blocked, broken or the like. When such a blockage or breakage occurs, accurate surgical operation may not be performed. Therefore, stop control is immediately performed of deactivating the laser treatment system 1. Owing to this, the laser treatment system 1 can have high safety and high reliability.

INDUSTRIAL APPLICABILITY

The present invention is usable for various devices for treating a living organism using laser light. Specifically, the present invention is usable for a device for performing a treatment and a surgical operation by use of laser light transmitted within a limited space, for example, an endoscope, while guiding various fluids in the limited space.

DESCRIPTION OF THE REFERENCE NUMERALS

12 . . . Operation unit
19 . . . Forceps insertion path
19a . . . Inner circumferential surface
19b . . . Inhalation guide path
21 . . . Endoscope tube
44 . . . Diseased part gas inhalation section
54 . . . Central control section
57 . . . Laser oscillation section
57a . . . Treatment laser light
59a . . . Assist gas
60a . . . Cooling water
62a . . . Diseased part treatment water
70 . . . Laser transmission path
75 . . . Cooling water circulation path
80, 180, 280, 380 . . . External tube
81 . . . Insertion space
82 . . . Outer circumferential convexed part
84 . . . Outer circumferential concaved part
84, 184, 284, 384 . . . Sub passage
84a, 184a, 284a, 384a . . . Assist gas sub passage
84b, 184b, 284b . . . Diseased part treatment water sub passage
84c, 184c, 284c, 384c . . . Cooling water recovery sub passage
85, 185, 285, 385 . . . Cooling water passage
90 . . . Hollow waveguide path
182 . . . Apex
183 . . . Side
382 . . . Arcked part at an end of the longer axis
383 . . . Arcked part at an end of the shorter axis

What is claimed is:

1. A laser transmission device for use in an endoscope having a treatment instrument channel comprising:
an external tube comprising:
a tube wall having an outer circumferential surface and an inner surface;
a plurality of convex parts and a plurality of concave parts arranged on the outer circumferential surface of the external tube at regular intervals;
a plurality of projections projecting inward in a radial direction from the inner surface of the external tube, located at an equal interval on the inner surface in a circumferential direction of the external tube; and
an insertion channel defined by the inner surface of the tube wall;
a hollow laser waveguide inserted into the external tube insertion channel; and
a plurality of fluid passages, wherein a first set of fluid passages are located inside the plurality of projections and another set of fluid passages are defined between an outer surface of the hollow laser waveguide and the inner surface of the external tube, wherein the laser transmission device is configured for insertion into the treatment instrument channel formed in a longitudinal direction of an external hose of the endoscope such that the plurality of convex parts contact an inner surface of the endoscope treatment instrument channel.

2. The laser transmission device according to claim 1, wherein the plurality of fluid passages are located between the hollow waveguide inserted into the insertion channel and an inner surface of the insertion channel, at an equal interval with respect to the inner surface.

3. The laser transmission device according to claim 1, wherein:

the external tube is inserted into the endoscope treatment instrument channel; and the external tube further comprises:

projections located at least at two positions as seen in a cross-section of the external tube, and projecting outward in a radial direction such that in the state where the external tube is inserted into the endoscope treatment instrument channel, tips of the projections are in contact with the inner surface of the endoscope treatment instrument channel; and gap formation parts for forming gaps together with the inner surface of the endoscope treatment instrument channel, the gaps being formed between adjacent projections of the at least two projections.

4. The laser transmission device according to claim 3, wherein:

the external tube includes the plurality of convex and concave parts so as to have a gear-like cross-section; and the convex and concave parts form the projections and the gap formation parts.

5. The laser transmission device according to claim 3, wherein:

the external tube has a polygonal cross-section; and apexes of the polygonal cross-section form the projections, and sides of the polygonal cross-section form the gap formation parts.

6. The laser transmission device according to claim 3, wherein:

the external tube has an elliptical cross-section; and arced parts at ends of a longer axis of the elliptical cross-section form the projections, and arced parts at ends of a shorter axis of the elliptical cross-section form the gap formation parts.

7. The laser transmission device according to claim 1, wherein one of the plurality of fluid passages is a cooling water channel for supplying cooling water for cooling the hollow waveguide path such that the cooling water flows in a direction in which the laser light is directed.

8. The laser transmission device according to claim 7, wherein one of the plurality of fluid passages which is different from the cooling water channel is a cooling water recovery channel for allowing the cooling water which has cooled the hollow waveguide to flow in a direction opposite to the direction in which the laser light is directed and thus recovering the cooling water.

9. The laser transmission device according to claim 7, wherein one of the plurality of fluid passages which is different from the cooling water channel is an irrigation channel for supplying irrigation water such that the irrigation water flows in the direction in which the laser light is directed and is released toward a diseased part.

10. The laser transmission device according to claim 7, wherein one of the plurality of fluid passages which is different from the cooling water channel is an assist gas channel for supplying assist gas such that the assist gas flows in the direction in which the laser light is directed and is released toward a diseased part.

11. A laser treatment tool, comprising:

a laser generation source;

a laser control section; and the laser transmission device according to claim 1.

12. A laser treatment tool, comprising:

a laser generation source;

a laser control section;

the laser transmission device according to claim 1;

a fluid inhalation unit connected to gap formation parts; and fluid absorption channels formed by the gap formation parts.

13. The laser treatment tool according to claim 11, wherein the laser light is carbon dioxide laser light.

14. The laser transmission path according to claim 1, wherein the external tube further comprises projections located at least at two positions as seen in a cross-section of the external tube, and projecting outward in a radial direction such that in the state where the external tube is inserted into the endoscope treatment instrument channel, tips of the projections are in contact with the inner surface of the endoscope treatment instrument channel; and gap formation parts for forming gaps together with the inner surface of the endoscope treatment instrument channel, the gaps being formed between adjacent projections of the at least two projections, and wherein each gap formation part comprises the fluid passage.

15. The laser transmission path according to claim 1, wherein the plurality of fluid passages are arranged inside the inner surface of the endoscope treatment instrument channel as another device channel for the endoscope in a radial direction of the external tube.

16. An external tube comprising:

a tube wall having an outer circumferential surface and an inner surface;

an insertion channel defined by the inner surface of the tube wall, that allows insertion of a hollow waveguide;

a plurality of projections projecting inward in a radial direction from the inner surface of the external tube, located at an equal interval on the inner surface in a circumferential direction of the external tube;

a plurality of fluid passages, wherein a first set of fluid passages are located inside the plurality of projections and another set of fluid passages are defined between an outer surface of the hollow waveguide path and the inner surface of the external tube; and a plurality of convex parts and a plurality of concave parts arranged on the outer circumferential surface of the external tube at regular intervals, wherein the external tube is configured to be included in a laser transmission device for use in an endoscope having a treatment instrument channel, the laser transmission device includes a hollow waveguide that guides laser light, the laser transmission device is configured for insertion into the treatment instrument channel formed in a longitudinal direction of an external hose of the endoscope such that the plurality of convex parts contact an inner surface of the endoscope treatment instrument channel.

17. The external tube according to claim 16, wherein the plurality of fluid passages are arranged inside the inner surface of the endoscope treatment instrument channel as another device channel for the endoscope in a radial direction of the external tube.

* * * * *